US009259502B2

(12) United States Patent
Butters et al.

(10) Patent No.: US 9,259,502 B2
(45) Date of Patent: Feb. 16, 2016

(54) UV REACTOR DESIGN HAVING PRESSURE EQUALIZING MANIFOLD FOR INCREASING UV FLUX EFFICIENCY

(76) Inventors: Brian E. Butters, London (CA); Anthony L. Powell, London (CA)

( * ) Notice: Subject to any disclaimer, the term of this patent is extended or adjusted under 35 U.S.C. 154(b) by 1061 days.

(21) Appl. No.: 12/785,298

(22) Filed: May 21, 2010

(65) Prior Publication Data

US 2010/0294726 A1 Nov. 25, 2010

Related U.S. Application Data

(60) Provisional application No. 61/180,336, filed on May 21, 2009.

(51) Int. Cl.
| | | |
|---|---|---|
| *C02F 1/32* | (2006.01) | |
| *C02F 1/30* | (2006.01) | |
| *A61L 9/20* | (2006.01) | |
| *C02F 1/00* | (2006.01) | |

(52) U.S. Cl.
CPC . *A61L 9/20* (2013.01); *A61L 9/205* (2013.01); *C02F 1/325* (2013.01); *C02F 1/006* (2013.01); *C02F 2201/3227* (2013.01)

(58) Field of Classification Search
CPC ............... C02F 2201/3225; C02F 2201/3227; C02F 1/32; C02F 1/30
USPC ............ 210/748.01, 747.3, 748.02, 748.03, 210/748.04, 748.05, 748.1, 748.11, 748.13, 210/748.14, 767; 422/24, 27, 28, 186, 422/186.3, 187; 250/432 R, 492.1, 494.1
See application file for complete search history.

(56) References Cited

U.S. PATENT DOCUMENTS

| | | | | |
|---|---|---|---|---|
| 4,336,223 A | * | 6/1982 | Hillman | 210/748.11 |
| 5,294,315 A | * | 3/1994 | Cooper et al. | 204/158.2 |
| 5,501,801 A | * | 3/1996 | Zhang et al. | 210/748.14 |
| 6,193,894 B1 | * | 2/2001 | Hollander | 210/748.11 |
| 7,800,310 B2 | * | 9/2010 | Butters et al. | 315/51 |
| 2009/0178968 A1 | * | 7/2009 | Cummins | 210/221.2 |

FOREIGN PATENT DOCUMENTS

| | | |
|---|---|---|
| CA | 2160915 C | 8/1995 |
| CA | 2513878 A1 | 8/2004 |

(Continued)

OTHER PUBLICATIONS

PCT/IB2010/001456, International Search Report and Written Opinion mailed Nov. 3, 2010.

*Primary Examiner* — Walter D Griffin
*Assistant Examiner* — Cameron J Allen
(74) *Attorney, Agent, or Firm* — Baker & McKenzie LLP

(57) ABSTRACT

The disclosed principles employ a UV reactor design for photo-based treatment of contaminated fluid media using a concentric single light source/single sleeve design, with multiple such concentric light source/sleeve units placed in parallel. In one embodiment, such a reactor may comprise an inlet manifold and an outlet manifold, and a plurality of tubular chambers connecting the inlet manifold to the outlet manifold. A plurality of such irradiating units are located within corresponding ones of the tubular chambers such that a fluid path is provided between each of the transparent sleeves and its corresponding tubular chamber where the contaminated fluid is irradiated as it passes through the chambers. The inlet ends of all of the chambers are connected to a single fluid intake manifold. This design allows the contaminated fluid pressure and flow to be evenly distributed among all of the fluid chambers via the intake manifold.

20 Claims, 5 Drawing Sheets

(56) References Cited

FOREIGN PATENT DOCUMENTS

| CA | 2596324 | A1 | | 8/2006 |
|---|---|---|---|---|
| WO | WO 9523766 | A1 | * | 9/1995 |
| WO | WO 2007025345 | A1 | * | 3/2007 |
| WO | WO 2007082337 | A1 | * | 7/2007 |
| WO | WO 2008039147 | A3 | * | 5/2008 |

* cited by examiner

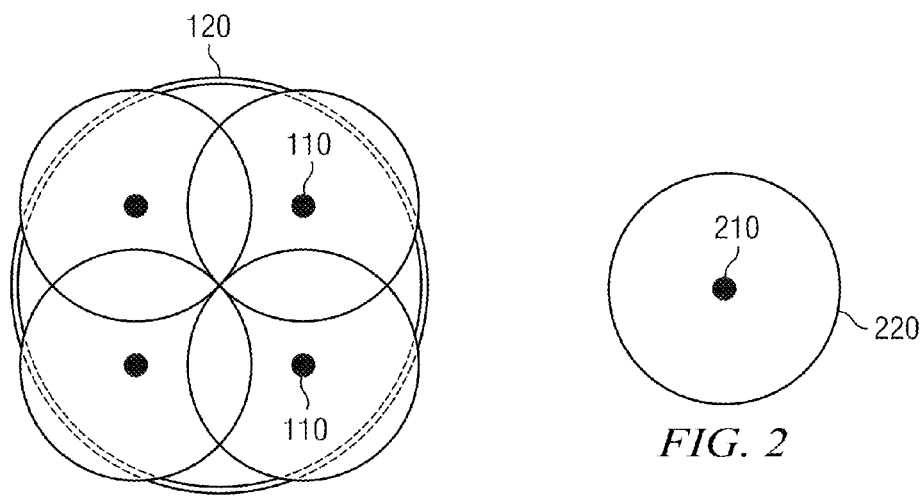
FIG. 1
(PRIOR ART)
FIG. 2
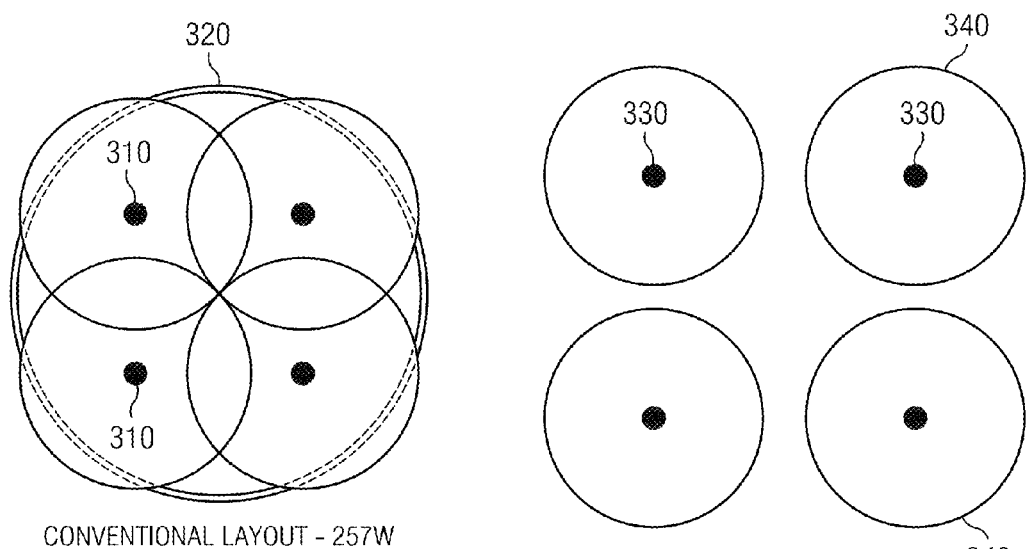
CONVENTIONAL LAYOUT - 257W
FIG. 3A
NOVEL LAYOUT - 180W
FIG. 3B

UV REACTOR DESIGN HAVING PRESSURE EQUALIZING MANIFOLD FOR INCREASING UV FLUX EFFICIENCY

PRIORITY CLAIM

This application claims the benefit of U.S. Provisional Patent Application Ser. No. 61/180,336, filed May 21, 2009, and entitled "UV REACTOR DESIGN HAVING PRESSURE EQUALIZING MANIFOLDS FOR INCREASING UV FLUX EFFICIENCY." This provisional application is incorporated by reference in its entirety.

BACKGROUND

While UV reactor designs, within which photolytic and photocatalytic decontamination of contaminated fluid media takes place, are plentiful, the up-scaling with regard to reactor size of UV reactors typically leads to significant reactor performance issues. As such, while small-scale reactors of various designs and layouts may work well, the same designs do not translate well into large-scale equipment. For example, conventional reactor designs that provide its contaminated media flow along a single, long chamber immediately suffer from size constraints of the equipment when up-scaled. Such reactors provide for the flow of contaminated media to be in a single chamber (i.e., in series) while a plurality of UV lamps are provided in parallel within this single flow chamber. West Besin's Trojan UV reactor is an example of this conventional design.

Within this type of reactor design, the parallel UV lamps illuminate in radiating circular patterns, as illustrated in FIG. 1. FIG. 1 shows the conventional design of multiple (e.g., four) UV lamps 110 placed in parallel within a single flow chamber 120. Because light radiates radially, FIG. 1 illustrates how in this conventional reactor chamber design, there are some spots ("blind spots") with no irradiation and other spots with overkill radiation (where irradiation overlaps) when using multiple lamps in parallel within a single flow chamber through which contaminated fluid media is passed. Accordingly, what is needed in the art is a reactor design having irradiated flow chambers that does not suffer from the deficiencies of the prior art designs.

SUMMARY

The disclosed principles employ a UV reactor design for photo-based (e.g., photocatalytic) treatment of contaminated fluid media using a concentric single light source/single sleeve design, with multiple such concentric light source/sleeve units placed in parallel. Conventional UV reactors employ multiple parallel lamps in single tube or sleeve, when looking at a cross-section of the reactor chamber. In contrast, the disclosed principles provides a reactor with multiple fluid chambers, where each chamber includes a transparent sleeve (typically quartz) housing a UV lamp, concentrically placed within the chamber. The inlet ends of all of the chambers are connected to a single fluid intake manifold, while the outlets ends of all of the chambers are connected to a single fluid outlet manifold. This design allows the contaminated fluid pressure and flow to be evenly distributed among all of the fluid chambers via the intake manifold, and then collecting the decontaminated fluid in a single outlet via the outlet manifold.

In one embodiment, a reactor constructed according to the disclosed principles for decontaminating contaminated fluid media may comprise an inlet manifold comprising a single fluid chamber, and an outlet manifold comprising a single fluid chamber. In addition, such a reactor may include a plurality of tubular chambers hermetically connecting the fluid chamber of the inlet manifold to the fluid chamber of the outlet manifold. Moreover, such a reactor may include a plurality of irradiating units each comprising an irradiation source within a transparent sleeve, where each of the irradiating units are located within corresponding ones of the plurality of tubular chambers such that a fluid path is provided between each of the transparent sleeves and its corresponding tubular chamber.

In another embodiment, a reactor according to the disclosed principles for decontaminating contaminated fluid media may comprise an inlet manifold comprising a fluid chamber, an outlet manifold comprising a fluid chamber, and a plurality of tubular chambers hermetically connecting the fluid chamber of the inlet manifold to the fluid chamber of the outlet manifold. Additionally, in such an embodiment, the reactor may also include a plurality of irradiating units each comprising a UV light source within a transparent sleeve, where each of the irradiating units are located within corresponding ones of the plurality of tubular chambers such that a fluid path is provided between each of the transparent sleeves and its corresponding tubular chamber. In such embodiments, the UV light sources are configured to irradiate UV light on the contaminated fluid as it passes through the fluid paths.

In other aspects, methods for decontaminating contaminated fluid media in accordance with the disclosed principles are also provided. In one embodiment, such a method may comprise feeding contaminated fluid into an inlet manifold comprising a single fluid chamber. Then, such a method may comprise passing the contaminated fluid through a plurality of tubular chambers hermetically connecting the fluid chamber of the inlet manifold to a fluid chamber of an outlet manifold. In such embodiments, each of the tubular chambers may comprise a corresponding one of a plurality of irradiating units therein, where each irradiating unit comprises an irradiation source within a transparent sleeve. The contaminated fluid is passed through fluid paths defined between each of the transparent sleeves and its corresponding tubular chamber. Then such an exemplary method may comprise irradiating the contaminated fluid with the irradiating sources while in the fluid paths.

BRIEF DESCRIPTION OF THE DRAWINGS

Embodiments are illustrated herein by way of example in the accompanying figures, in which like reference numbers indicate similar parts, and in which:

FIG. 1 illustrates the conventional design of multiple (e.g., four) UV lamps 110 placed within a single flow chamber 120;

FIG. 2 illustrates the irradiation pattern of a UV reactor chamber design, where a single lamp 210 is concentrically located within the flow tube 220 where contaminated fluid media is passed;

FIG. 3A illustrates the conventional layout when four UV lamps 310 are employed in a single flow chamber 320 having the conventional parallel lamp approach;

FIG. 3B illustrates the multiple flow chamber 340 with four UV lamps 330 in four distinct flow chambers in accordance with the disclosed principles;

DETAILED DESCRIPTION

Figure 4:
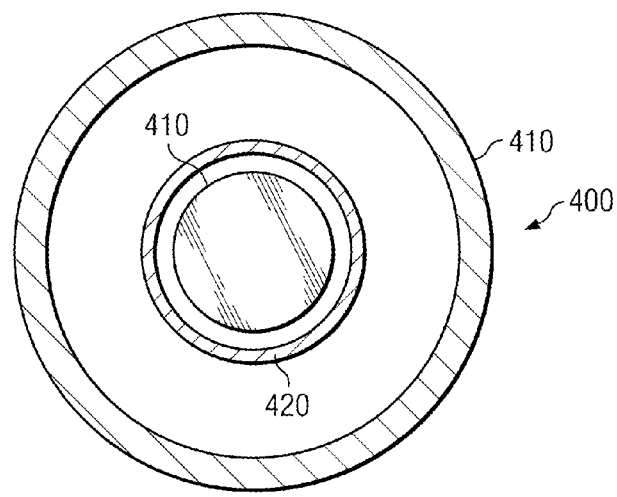
FIG. 4 illustrates a more detailed cross-sectional view of a lamp unit 400, as is used with a reactor constructed according to the disclosed principles.

In response to the inefficiency of this conventional UV reactor design, the use of a single UV lamp in a single tube was developed by the present inventors. FIG. 2 illustrates the irradiation pattern of such a UV reactor chamber design, where a single lamp 210 is concentrically located within the flow tube 220 where contaminated fluid media is passed. This singular concentric design has obvious benefits over multiple parallel lamps located within a single tube, particularly with regard to the total radiation area.

FIG. 3 illustrates the Power vs. Constant Flux in laminar flow when four UV lamps 310 are employed in a single flow chamber 320 having the conventional parallel lamp approach, versus four UV lamps 330 employed in the concentric, multiple flow chamber 340 approach developed by the present inventors. More specifically, four lamps are employed in each reactor design to irradiate the same area, where in the conventional reactor design a single flow chamber is used, while in the reactor constructed according to the disclosed principles, four distinct flow chambers are used. In the presently disclosed reactor, the lamps 330 are concentric within the four flow tubes 340. As can be seen in FIG. 3, the concentric flow tube reactor chamber design disclosed herein is more efficient since none of the UV radiation crosses into another lamp's path. For example, in the conventional reactor design, a combined 257 Watts is used in an attempt to irradiate the single flow chamber, while four 45 Watt lamps, for a total of only 180 Watts, are used to irradiate the same amount of flow area in the disclosed reactor design. This is because in the conventional reactor design, the lamps 310 must radiate more light, resulting in some overlapping radiation as well as excess radiation lost through the quartz sleeve, in order to try to irradiate the entirety of the single flow chamber. Consequently, this is a 30% power reduction for the disclosed reactor design, as well as 16% lower sleeve transmission loss.

Based on the all of the above, the up-scaling of a UV reactor in terms of size alone results in large increases in sheer manufacturing costs with regard to both materials and manufacturing time, sometimes to the point of being cost prohibitive and typically resulting in an overall less efficient reactor. In addition, up-scaling not in terms of mere size, but in terms of processing capabilities creates additional problems in the conventional approaches. The disclosed principles employ the efficient single UV lamp concentric design in a much larger scale in terms of processing capability, and the result is a reactor far smaller in overall size than conventional UV reactors, yet far more efficient in terms of the amount of contaminated media it processes. Specifically, the constant flux in a reactor designed in accordance with the disclosed principles overcomes the deficiencies, e.g., the "blind spots" in conventional reactors. This eliminates the need to over power the reactor, as is done in conventional reactors, in order to compensate for blind spots (as illustrated above in FIGS. 1 and 3), as well as the need for computational fluid dynamics when the disclosed single concentric reactor design is used. Thus, the disclosed principles result in a UV reactor design with greater efficiency in the manufacturing of the reactor, but also greater efficiency in UV flux based on the ability to employ less wattage during operation.

The present inventors have previously filed patent applications involving small annular designs within UV reactors for photo-based treatment of fluid contaminated media, as well as for end-to-end assemblies for UV lamps used in such reactors and the in-situ cleaning of the sleeves surrounding such UV lamps without the use of conventional wipers on the sleeves. For example, see U.S. Pat. No. 5,462,674, U.S. patent application Ser. No. 12/053,161, and U.S. Pat. No. 7,425,272, all of which are commonly assigned with the present disclosure and which are incorporated herein by reference in their entirety. The disclosed principles may be employed with one or more of these technologies, or independently.

FIG. 4 illustrates a more detailed cross-sectional view of a lamp unit 400, as is used with a reactor constructed according to the disclosed principles. The lamp unit 400 includes a single, concentric UV lamp 410 surrounded by a transparent sleeve 420. The sleeve may be constructed out of quartz or other similar material. The lamp 410 and sleeve 420 are then concentrically located within a single chamber 430. As discussed in detail in the present inventors' U.S. Pat. No. 7,425,272, the single lamp/single sleeve concentric design provides efficient irradiation of contaminated fluid media flowing in the annulus defined between the sleeve 420 and the interior of the chamber 430.

Moreover, as also discussed in the U.S. Pat. No. 7,425,272, the small annular space between the sleeve 420 and the interior of the wall of the chamber 430 used in the UV reactors can beneficially be used to keep the quartz sleeves 420 clean without the use of wipers. More specifically, high turbulence and high flow rate, combined with certain photocatalytic decontamination additives can exploit the abrasive nature of the additives to hone to the surfaces of the sleeves 420 and remove contamination build-ups that typically occurs in conventionally designed reactors. In exemplary embodiments, the annular space between the sleeve 420 and the chamber 430 is only about 1 mm, but other sizes for the annular space are also possible.

Figure 5:
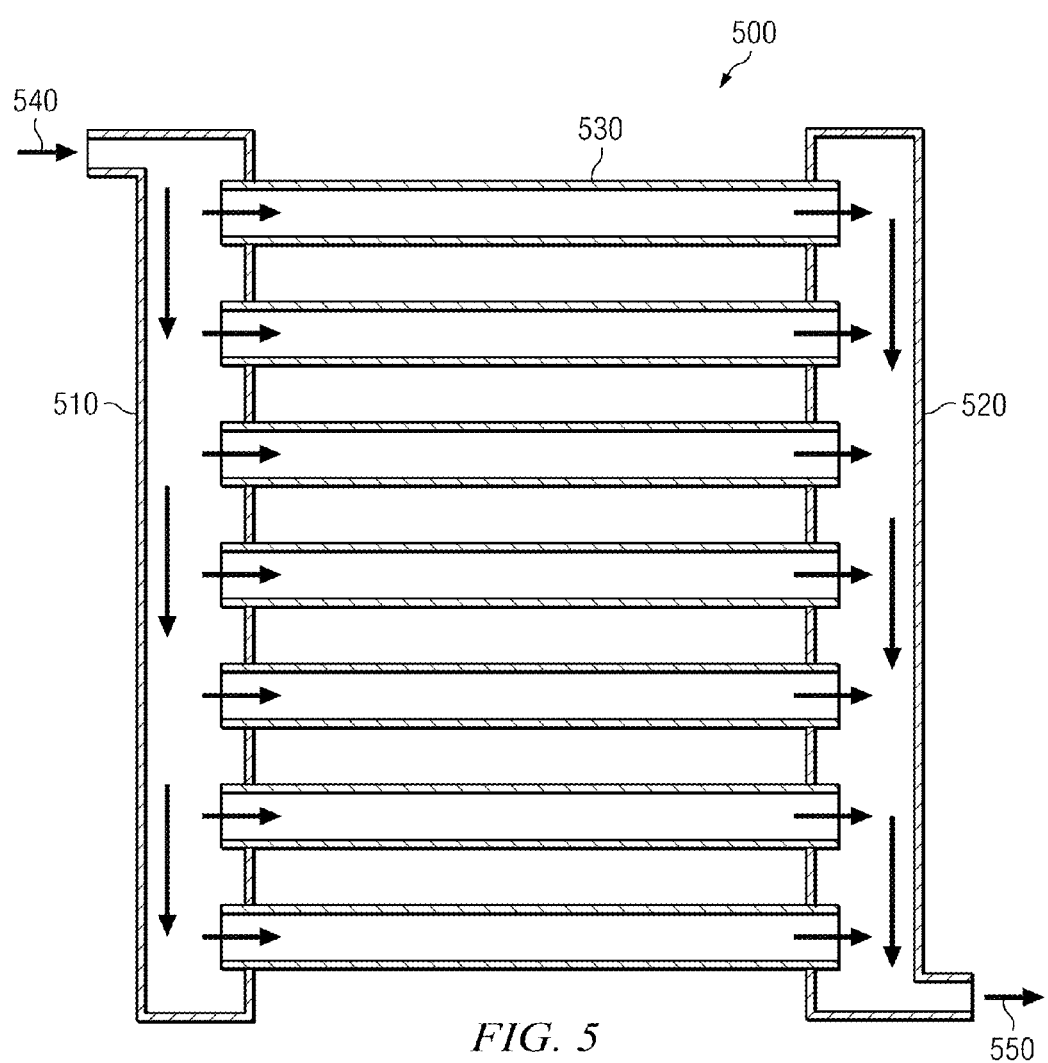
FIG. 5 illustrates a simplified block diagram of one embodiment of a UV reactor 500 designed with manifolds in accordance with the disclosed principles.

FIG. 5 illustrates a simplified block diagram of one embodiment of a UV reactor 500 designed with manifolds in accordance with the disclosed principles. More specifically, the reactor includes an inlet manifold 510 and an outlet manifold 520, and a plurality of UV chambers 530 connected between the two manifolds 510, 520. As discussed above, each of the chambers 530 includes a concentric UV lamp and transparent sleeve mounted within each chamber 530, where the fluid media flows from the inlet manifold 510, through the annulus between the sleeve and the chamber wall, and out through the outlet manifold 520. Therefore, the inlet and outlet manifolds 510, 520 allow for incoming 540 and outgoing 550 fluid flows to be equalized across all of the chambers 530 included in the reactor 500. As the contaminated fluid flows through the fluid paths defined by the annular areas, the irradiation causes a photocatalytic reaction in the contaminated fluid (using the photocatalyst) whereby decontaminated effluents are rendered in the fluid. Accordingly, the concentric design of each chamber 530 allows for less overall power usage when the passing contaminated fluid is irradiated as compared to conventional reactor designs, such as the single-chamber reactor discussed above. A filter may then be used to filter the decontaminated effluents rendered in the fluid. Moreover, the decontaminated effluents may also be recovered using appropriate techniques depending on the type of contaminant.

Figure 6:
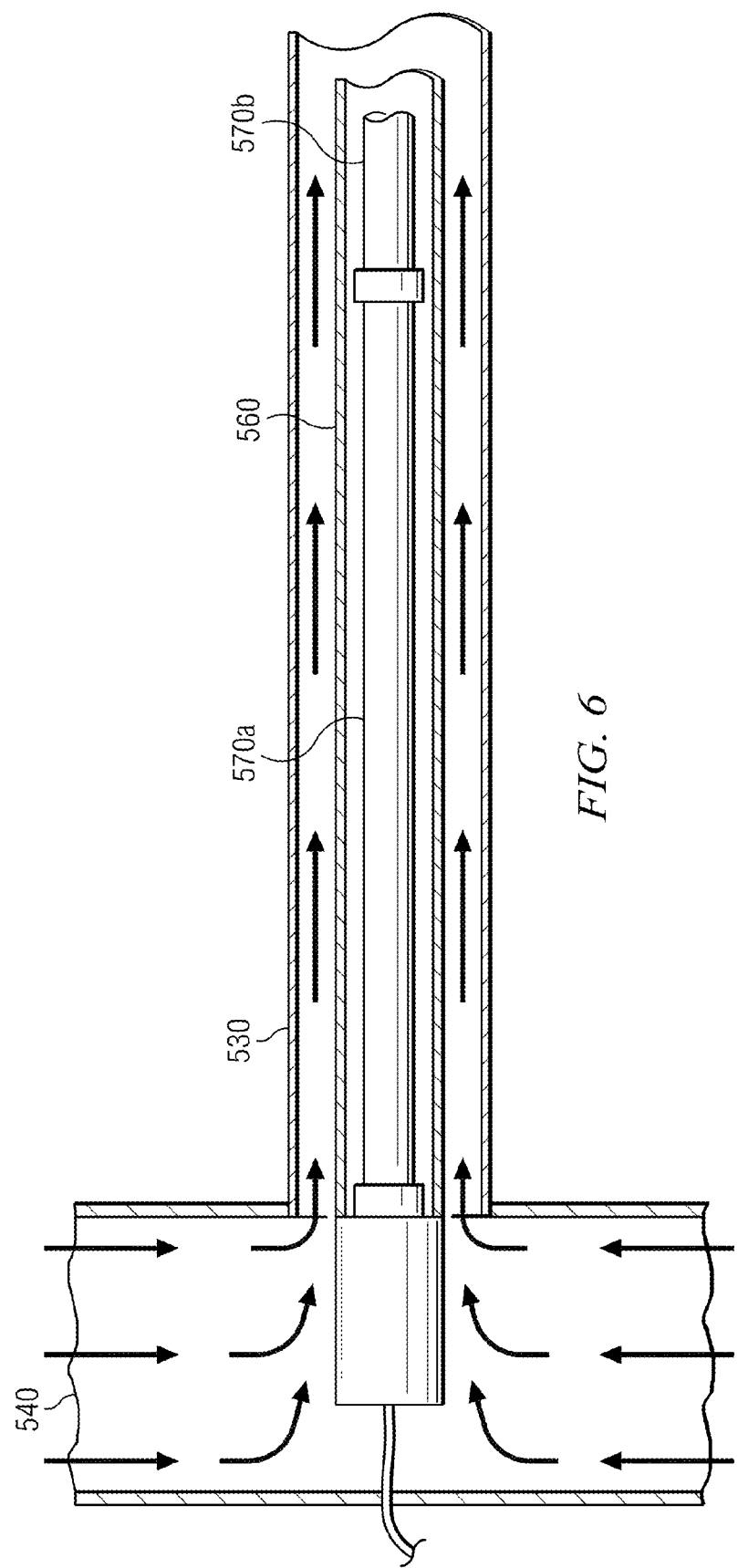
FIG. 6 illustrates a close up cross-sectional view of one of the UV chambers 530 in the reactor 500 illustrated by FIG. 5.

FIG. 6 illustrates a close up cross-sectional view of one of the UV chambers 530 in the reactor 500 illustrated in FIG. 5.

Within the chamber 530, the transparent sleeve 560 concentrically located within the chamber 530 can be seen. Within the transparent sleeve 560 are two UV lamps 570a and 570b, also concentrically positioned. Specifically, in some embodiments, two (or more) UV lamps 570a, 570b may be connected end-to-end within the transparent sleeve 560 to provide the irradiation of the inflowing contaminated fluid media 540. Such an end-to-end lamp assembly is described in further detail in co-pending patent application Ser. No. 12/053,161, identified above. Of course, other type and numbers of UV lamps 570a, 570b may also be employed with a reactor 500 constructed according to the disclosed principles.

Based on the above, one significant advantage of a UV reactor 500 design according to the disclosed principles is that there is no pressure drop across the chambers 530 because the entire manifolds are open to the entire set of chambers 530. However, the contaminated fluid still flows through the individual concentric UV lamp chambers 530 through the small annular spaces described above. Thus, the fluid media is decontaminated efficiently in series through the individual lamps/sleeves, but at a large scale through the multiple chambers 530 connected in parallel by the manifolds 510, 520. The net result of the disclosed principles is a UV reactor 500 with a larger processing capability (throughput flow-rate) than conventionally designed reactors with lamps connected in parallel in a single flow chamber. Additionally, the novel reactor 500 achieves the increasing processing efficiency in a much smaller overall size.

Figure 7:
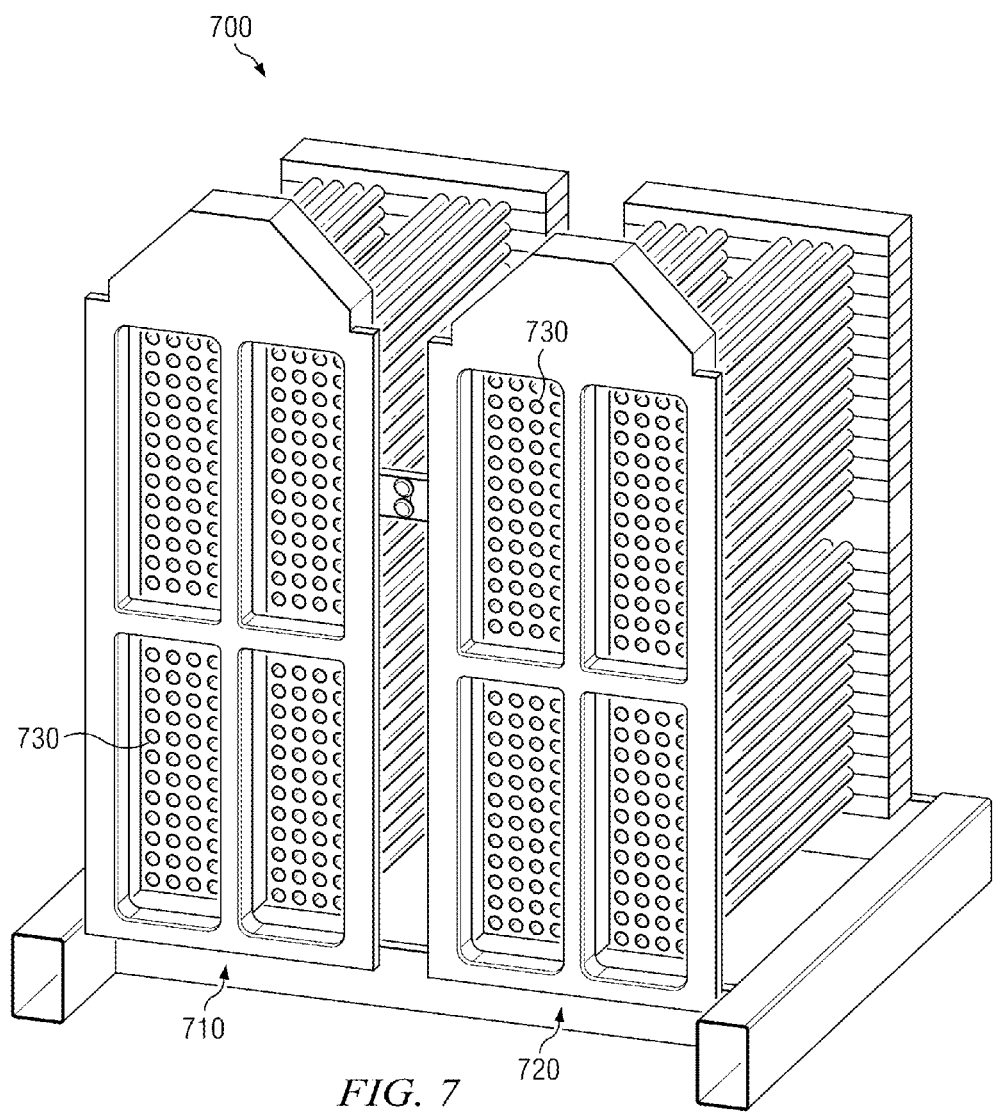
FIG. 7 illustrates the interior of the inlet and outlet manifolds of an embodiment of a UV reactor 700 constructed according to the disclosed principles.

FIG. 7 illustrates the interior of the inlet and outlet manifolds of an embodiment of a UV reactor 700 constructed according to the disclosed principles. In the embodiment illustrated in FIG. 7, the inlet manifold 710 is shown on the left side, while the outlet manifold 720 is shown on the right side. The numerous circular openings 730 shown in FIG. 7 are hollow tubes that extend from the front to the back of the reactor 700. These tubes are the chambers 730 that house the sleeves and UV lamps when inserted therein. During a decontamination operation, contaminated fluid media is pumped into the inlet manifold 710 until it fills. Then the continued pressure on the fluid forces the contaminated fluid through the parallel-connected chambers 730 having the sleeves/lamps therein. On the opposite side of this reactor 700, another manifold (not illustrated), in one embodiment, may be provided to connect the two "halves" of the reactor. With this type of configuration, the inlet and outlet of the reactor 700 are on the same side, whereas in the embodiment shown in FIG. 5, the inlet and outlet of that reactor 500 were on opposite sides of the reactor 500.

In certain embodiments, a reactor constructed according to the disclosed principles is constructed so that it does not have welded tubes/chambers. More specifically, if multiple chambers are employed in a reactor of the type illustrated in FIG. 7, the housing of the reactor is typically stainless steel in order to resist corrosion from the contaminated fluid flowing therethrough. Accordingly, some may choose to weld the ends of the tubes in such reactors to seal their connection. However, in advantageous embodiments in accordance with the disclosed principles, the tubes or chambers are press-fit into the manifold to eliminate welding. In practice, while eliminating welding, a reactor such as the type illustrated in FIG. 7 has maintained steady pressure at 150 p.s.i. without leaks using such press-fitting of the chambers.

Numerous advantages are had by such press-fit embodiments. For example, the construction time of the reactor is substantially lessened since the chambers and manifolds do not need to be sent out for welding. This also reduces manufacturing costs. Even if welding could be done in-house, the time required to weld each tube to the manifolds at both ends is substantially longer than the time required to simply press-fit the tube through the interior manifold wall. This is especially true when water-tight welds are required, as they are in UV reactors used for decontaminating fluid media.

Figure 8:
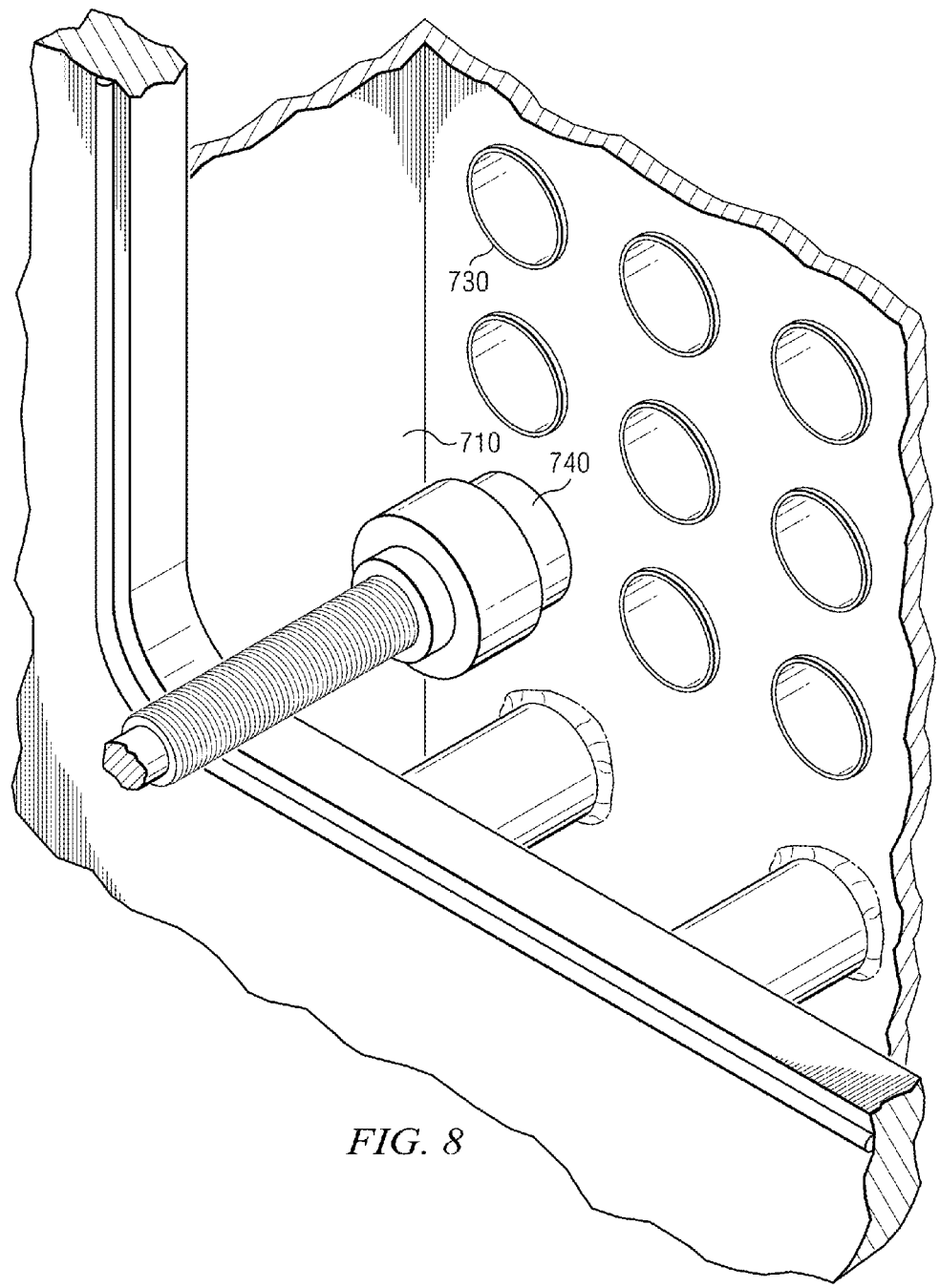
FIG. 8 illustrates a close-up view of the interior of the inlet manifold 710 of the UV reactor 700 illustrated in FIG. 7.

FIG. 8 illustrates a close-up view of the interior of the inlet manifold 710 of the UV reactor 700 illustrated in FIG. 7. In this close up view, one of the UV lamp/sleeve units 740 can be seen being inserted into one of the chambers 730 in accordance with the disclosed principles. Such lamps/sleeves 740 are inserted into all of the remaining chambers 730, and then the manifold 710 is sealed up so that the contaminated fluid may be fed into the reactor 700 for decontamination by flowing within each of the chambers 730 and around each chamber's inserted sleeve/lamp 740.

The close up view of FIG. 8 also shows the lack of welds around each of the chambers 730, where they are connected to the manifold 710 wall. Another advantage of eliminating the welding allows for tighter packing density of the chambers 730. This is the case since there is no need to weld around the edges of the chambers 730 where they meet the walls manifolds 710, 720. Moreover, as mentioned above, stainless steel is typically used to construct the reactor 700, in this case including the manifolds 710, 720. When stainless steel is welded, however, it tends to warp significantly. With as many welds as would be needed to secured the numerous chambers 730 in place between the manifolds 710, 720, the interior walls of the manifolds 710, 720 would typically be badly warped once all of the welds are finished.

Still further, providing a water-tight seal with stainless steel welding is difficult when compared to iron-based steels, and is typically a very time-consuming task. Although the stainless material itself does not tend to corrode, the weld beads when even welding stainless steel can have significant impurities and/or non-stainless steel materials therein. These impurities and other materials, which originate from the alloy (i.e., not pure stainless steel) welding rods and flux needed used to weld stainless steel, and thus the weld beads (stress locations) are where corrosion typically occurs. Thus, eliminating the welds significantly improves the corrosion tolerance of a UV reactor constructed according to the disclosed principles. Such corrosion resistance is particularly beneficial for applications such as sea water purification/decontamination, etc.

Based on the above disclosure, the disclosed principles provide a UV reactor with significant size and efficiency improvements over conventional reactor designs. In addition to the advantages discussed above, when a reactor constructed according to the disclosed principles is compared with a conventional parallel lamp (within a single chamber) design like the Trojan reactor discussed above, the disclosed reactor provides a far greater reactor footprint vs. power advantage. For example, a current UV reactor constructed according to the disclosed principles, such as the reactor 700 illustrated in FIGS. 7 and 8, has a footprint of a mere 2.5 ft×5.5 ft per unit. Even when multiple lamps are used for each chamber of a reactor constructed as disclosed herein, these lamps are still connected end-to-end in series, and thus are sequential within the same chamber. Thus, the cross-section of each chamber has only a single lamp at a time. Accordingly, a UV reactor constructed as disclosed herein provides the power of multiple lamps, but in a much more efficient manner since they are in connected in series within a much smaller chamber, not in parallel within a larger chambers as found in conventional reactors.

While various embodiments in accordance with the disclosed principles have been described above, it should be understood that they have been presented by way of example only, and are not limiting. Thus, the breadth and scope of the invention(s) should not be limited by any of the above-described exemplary embodiments, but should be defined only in accordance with the claims and their equivalents issuing from this disclosure. Furthermore, the above advantages and features are provided in described embodiments, but shall not limit the application of such issued claims to processes and structures accomplishing any or all of the above advantages.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically, a description of a technology in the "Background" is not to be construed as an admission that technology is prior art to any invention(s) in this disclosure. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings herein.

What is claimed is:

1. A reactor for decontaminating contaminated fluid media, the reactor comprising:
   an inlet manifold comprising a single fluid chamber;
   an outlet manifold comprising a single fluid chamber;
   a plurality of parallel tubular chambers hermetically connecting the fluid chamber of the inlet manifold directly to the fluid chamber of the outlet manifold; and
   a plurality of irradiating units each comprising an irradiation source within a transparent sleeve, each of the irradiating units concentrically located within corresponding ones of the plurality of tubular chambers such that a fluid path is provided between each of the transparent sleeves and its corresponding tubular chamber, the fluid paths configured to pass a contaminated fluid therethrough in one common direction.

2. A reactor according to claim 1, wherein the irradiating source in the irradiating units comprises a UV lamp.

3. A reactor according to claim 2, wherein the irradiating source in the irradiating units comprises a plurality of UV lamps connected end-to-end.

4. A reactor according to claim 1, wherein the transparent sleeves of the irradiating units comprise quartz sleeves.

5. A reactor according to claim 1, wherein the irradiating sources irradiate the annular space between the transparent sleeves and the tubular chambers.

6. A reactor according to claim 5, wherein the contaminated fluid comprises a photocatalyst, and wherein the irradiating sources irradiate the annular space between the transparent sleeves and the tubular chambers sufficient to bring about a photocatalytic reaction in the contaminated fluid whereby decontaminated effluents are rendered in the fluid.

7. A reactor according to claim 6, further comprising a filter for segregating the decontaminated effluents by filtration.

8. A reactor according to claim 1, wherein the fluid paths each measure about 1 mm.

9. A reactor for decontaminating contaminated fluid media, the reactor comprising:
   an inlet manifold comprising a fluid chamber;
   an outlet manifold comprising a fluid chamber;
   a plurality of parallel tubular chambers hermetically connecting the fluid chamber of the inlet manifold directly to the fluid chamber of the outlet manifold; and
   a plurality of irradiating units each comprising a UV light source within a transparent sleeve, each of the irradiating units concentrically located within corresponding ones of the plurality of tubular chambers such that a fluid path is provided between each of the transparent sleeves and its corresponding tubular chamber, wherein the fluid paths are configured to pass a contaminated fluid therethrough in one common direction, and wherein the UV light sources are configured to irradiate UV light on the contaminated fluid as it passes through the fluid paths.

10. A reactor according to claim 9, wherein the UV light source in the irradiating units comprises a plurality of UV lamps connected end-to-end.

11. A reactor according to claim 9, wherein the transparent sleeves of the irradiating units comprise quartz sleeves.

12. A reactor according to claim 9, wherein the contaminated fluid comprises a photocatalyst, and wherein the UV light sources irradiate the annular space between the transparent sleeves and the tubular chambers sufficient to bring about a photocatalytic reaction in the contaminated fluid whereby decontaminated effluents are rendered in the fluid.

13. A reactor according to claim 12, further comprising a filter for segregating the decontaminated effluents by filtration.

14. A reactor according to claim 9, wherein the fluid paths each measure about 1 mm.

15. A reactor according to claim 1, wherein each of the tubular chambers comprises a first end that makes direct contact with the inlet manifold and a second end, opposite to the first end, that makes direct contact with the outlet manifold.

16. A reactor according to claim 1, wherein the contaminated fluid, en route from the fluidic chamber of the inlet manifold to the fluidic chamber of the outlet manifold, travels no more than the length of one tubular chamber.

17. A reactor according to claim 1, wherein the tubular chambers are press-fit into the inlet manifold and into the outlet manifold.

18. A reactor for decontaminating contaminated fluid media, the reactor comprising:
   an inlet manifold comprising a single fluid chamber;
   an outlet manifold comprising a single fluid chamber;
   a plurality of parallel tubular chambers hermetically connecting the fluid chamber of the inlet manifold directly to the fluid chamber of the outlet manifold, each of the tubular chambers comprising a first end that touches the inlet manifold and a second end, opposite to the first end, that touches the outlet manifold; and
   a plurality of irradiating units each comprising an irradiation source within a transparent sleeve, each of the irradiating units concentrically located within corresponding ones of the plurality of tubular chambers, each of the transparent sleeves and its corresponding tubular chamber together defining an annular flow path, the annular flow path configured to pass a contaminated fluid therethrough in one common direction.

19. A reactor for decontaminating contaminated fluid media, the reactor comprising:
   an inlet manifold comprising a fluid chamber;
   an outlet manifold comprising a fluid chamber;
   a plurality of parallel tubular chambers hermetically connecting the fluid chamber of the inlet manifold directly to the fluid chamber of the outlet manifold, the tubular chambers being arranged in a plurality of layers, each layer comprising at least eight tubular chambers; and a plurality of irradiating units each comprising a UV light source within a transparent sleeve, each of the irradiating units concentrically located within corresponding ones of the plurality of tubular chambers, each of the transparent sleeves and its corresponding tubular chamber together defining an annular flow path, wherein the UV light sources are configured to irradiate UV light on the contaminated fluid as it passes through the fluid paths.

20. A reactor according to claim 19, wherein the tubular chambers are press-fit into the inlet manifold and into the outlet manifold so as to maintain a steady pressure at 150 pounds per square inch (p.s.i.) or higher without leaks.

* * * * *